(12) United States Patent
Jarrelle et al.

(10) Patent No.: US 10,188,474 B2
(45) Date of Patent: Jan. 29, 2019

(54) SKIN-TO-SKIN CONTACT OBSTETRICAL SURGICAL DRAPE

(71) Applicant: Clever Medical, Sanford, FL (US)

(72) Inventors: Kimberly Jarrelle, Moseley, VA (US); Deborah Burbic, Glen Allen, VA (US); Jessamine Niccoli, North Chesterfield, VA (US)

(73) Assignee: CLEVER MEDICAL, Sanford, FL (US)

( * ) Notice: Subject to any disclaimer, the term of this patent is extended or adjusted under 35 U.S.C. 154(b) by 399 days.

(21) Appl. No.: 14/302,912

(22) Filed: Jun. 12, 2014

(65) Prior Publication Data

US 2015/0359596 A1 Dec. 17, 2015

(51) Int. Cl.
*A61B 19/08* (2006.01)
*A61B 46/00* (2016.01)
*A61B 46/20* (2016.01)
*A41D 13/12* (2006.01)
*A61B 17/00* (2006.01)

(52) U.S. Cl.
CPC .............. *A61B 46/00* (2016.02); *A61B 46/20* (2016.02); *A61B 46/30* (2016.02); *A41D 13/1236* (2013.01); *A61B 2017/00902* (2013.01)

(58) Field of Classification Search
CPC ......... A61B 46/00; A61B 46/10; A61B 46/13; A61B 46/20; A61B 46/30; A61B 46/40; A61B 46/23; A61B 46/27; A61B 19/00; A61B 19/08; A61B 19/10; A41D 13/12; A41D 13/1209; A41D 13/1236
USPC ....................... 128/849, 853, 854; 5/482, 486
See application file for complete search history.

(56) References Cited

U.S. PATENT DOCUMENTS

| 1,724,443 | A | | 8/1929 | Wheller |
| 3,799,161 | A | * | 3/1974 | Collins ................. A61B 19/08 128/854 |
| 3,826,253 | A | * | 7/1974 | Larsh .................... A61B 19/08 128/854 |
| 4,027,665 | A | | 6/1977 | Scrivens |
| 4,196,723 | A | | 4/1980 | Moose |

(Continued)

FOREIGN PATENT DOCUMENTS

GB 2477814 A 8/2011

OTHER PUBLICATIONS (Clever Medical) "Stephanie's Immediate Skin to Skin Experience" Youtube Video Screenshot. (Applicants note that a screenshot to this YouTube was cited in the International Search Report (ISR) and Written Opinion dated Oct. 8, 2015. A screenshot of this video taken on Dec. 20, 2016 is included herewith, showing the title of the video, the upload date of Jun. 12, 2015, the uploader as Clever Medical, and the same URL cited in the ISR https://www.youtube.com/watch?v=JSNrnRXVEeQ).

(Continued)

*Primary Examiner* — Keri J Nelson
(74) *Attorney, Agent, or Firm* — Fay Sharpe LLP

(57) ABSTRACT

A fenestration drape and a method for providing skin-to-skin contact of a newborn with the mother immediately after birth during a Cesarean delivery are provided. The fenestration drape includes a portal which may be opened and reclosed without compromise to the sterile barrier. The method facilitates the critical contact without interruption and with continuity of sterile field throughout the procedure.

20 Claims, 5 Drawing Sheets

(56) References Cited

U.S. PATENT DOCUMENTS

| | | | |
|---|---|---|---|
| 4,316,456 A | 2/1982 | Stoneback | |
| 4,489,720 A | 12/1984 | Morris | |
| 5,109,873 A * | 5/1992 | Marshall | A61B 19/08 |
| | | | 128/849 |
| 5,209,243 A | 5/1993 | Glassman | |
| 5,464,024 A | 11/1995 | Mills | |
| 5,515,868 A | 5/1996 | Mills | |
| 5,538,012 A * | 7/1996 | Wiedner | A61B 19/08 |
| | | | 128/849 |
| 5,592,952 A * | 1/1997 | Bohn | A61B 19/08 |
| | | | 128/849 |
| 6,843,252 B2 * | 1/2005 | Harrison | A61B 46/00 |
| | | | 128/849 |
| 7,610,918 B2 | 11/2009 | Bowen | |
| 8,011,371 B2 | 9/2011 | Rotolo | |
| 2010/0192960 A1 * | 8/2010 | Rotolo | A61B 19/08 |
| | | | 128/854 |
| 2010/0222725 A1 * | 9/2010 | Munzel | A47H 99/00 |
| | | | 602/3 |
| 2011/0030702 A1 | 8/2011 | Czajka | |
| 2012/0222686 A1 | 9/2012 | Lockwood | |
| 2013/0247921 A1 * | 9/2013 | Dye | A61B 19/08 |
| | | | 128/853 |

OTHER PUBLICATIONS

International Search Report and Written Opinion dated Oct. 8, 2015.

* cited by examiner

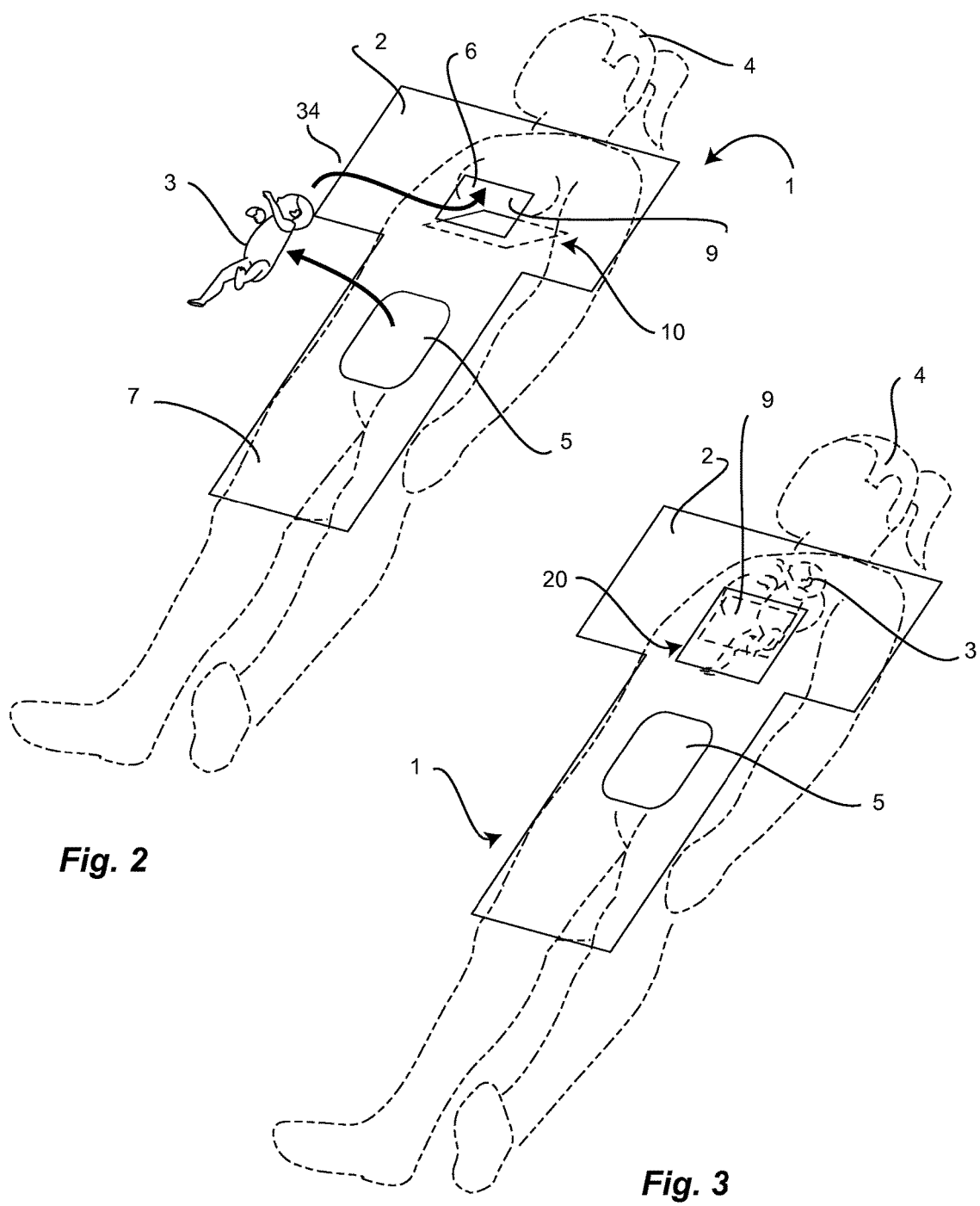

SKIN-TO-SKIN CONTACT OBSTETRICAL SURGICAL DRAPE

This is a U.S. Non-Provisional Patent Application.

FIELD OF THE INVENTION

This invention relates to surgical fenestration drapes, and more particularly to surgical drapes used in Cesarean-Section procedures.

BACKGROUND OF THE INVENTION

Transition from the intra-uterine environment to extra-uterine life is a dynamic, yet stressful, event for the fetus. Similarly, the critical physiological, neuro-behavioral and regulatory changes which must occur immediately after birth also result in significant neonatal stress. The multiple changes during this sensitive period necessitate significant neonatal adaptations during a very short time-period. Evidence documented in recent scientific reports and research studies, however, suggests that the neonate, or newborn, needs "only the mother" to make an optimal transition during this highly stressful and sensitive period. In fact, skin-to-skin-contact (SSC) between the mother and infant during the immediate post-delivery period mitigates stress associated with the birthing process, facilitates neonatal autonomic, regulatory, motor, and interactive adaptation, and eases overall fetal transition to extra-uterine life. Moreover, evidence suggests that both short-term and long-term benefits result from adoption of this "natural" practice.

Multiple benefits of adopting SSC during the immediate post-delivery period have been documented in the literature:

1. SSC mediates the neonatal stress response and promotes physiological regulation and stabilization:
   a. Facilitates neonatal thermo-regulation;
   b. Facilitates neonatal cardio-pulmonary stability;
   c. Increases neonatal sleep organization;
   d. Promotes earlier glucose regulation;
   e. Facilitates greater relaxation and reduces crying; and
   f. Promotes analgesia during invasive procedures.
2. SSC is associated with early initiation and longer duration of breastfeeding:
   Breast milk is the optimal source of nutrition and source of natural immunity for the infant. Currently-accepted evidence-based recommendations regarding breastfeeding indicate that this practice should be initiated within 30-60 minutes after delivery (American Association of Pediatrics, 2012; BFHI, 2009). Immediate mother-infant SSC after delivery has been associated with the following benefits:
   a. Increased ability of the neonate to recognize the mother's milk;
   b. A higher rate of successful initiation of breastfeeding;
   c. A longer duration of breastfeeding; and
   d. Higher prevalence of timely neonatal metabolic/glucose regulation;
3. SSC is associated with positive infant developmental and social benefits:
   a. Increased maternal-infant interaction; maternal affection, facilitates bonding;
   b. Greater tactile and verbal stimulation of the infant by the mother;
   c. Vocal parental-infant interaction after birth; and
   d. Greater prevalence of future mother-infant attachment.
4. Multiple maternal benefits have also been documented:
   a. Release of oxytocin which facilitates control of bleeding in immediate post-partum period;
   b. Increased reported maternal satisfaction and positive feelings;
   c. Increased reported maternal feelings of relaxation and well-being;
   d. Decreased reported maternal anxiety and stress;
   e. Higher reported breastfeeding self-efficacy and overall confidence with breastfeeding;
   f. Increased reported maternal sensitivity to the infant; increased maternal affection and attachment; and
   g. Fewer reported post-partum depressive symptoms.

The rate of Cesarean delivery has risen markedly in the near past. In fact, according to the most recent statistics from the U.S. Center for Disease Control and Prevention (CDC, 2014), the current Cesarean delivery rate in the U.S. has risen to 32.8% of all deliveries. Furthermore, in spite of the compelling evidence in support of initiating SSC between the mother and infant immediately after birth, the adoption of this practice is limited to the period after Cesarean delivery, not during delivery. Thus, a significant number of mother-infant dyads are denied the opportunity for a widely-accepted standard of care that facilitates both short-term and long-term physiological, psychological, social and developmental adaptation of the baby and mother.

Because of the different routines required in the operating room due the highly controlled environment for the surgical procedure, the lower room temperature in the operating suite, the close surveillance of the mother required by the anesthesiologist during the operative procedure, and the sterile operative field environment, many misperceptions, fears and lack of understanding among healthcare providers commonly exist regarding the standard of care for SSC. These misperceptions and fears create many challenges to the adoption of SSC. Thus, it is common practice in the operating suite for the neonate to be placed under a radiant warmer and swaddled or transported directly to the nursery. All of these options result in the delay of immediate bonding between mother and her neonate.

One significant barrier to SSC immediately after birth in the operating suite is the physical barrier between the mother and her newly delivered baby created by the sterile field. The sterile field must be maintained throughout the Cesarean procedure, which includes, in addition to the delivery, the post-delivery wound closing and dressing. The present state of art in the field of fenestration drapes lacks an effective means to bridge the sterile field to access the mother's skin immediately upon delivery without, at the same time, compromising the sterile barrier.

SUMMARY OF THE INVENTION

The present invention is a novel surgical drape devised to overcome this barrier. This innovative drape allows the obstetrician to reach through a pre-designed portal in the main drape to place the infant on the mother's chest immediately after delivery without compromising sterility.

It is an object of the present invention, therefore, to provide skin-to-skin contact between a mother and her newborn as close to immediately upon delivery as possible during a Cesarean procedure. It is a further object to provide a portal through a surgical drape to be used in a Cesarean procedure, apart from the necessary surgical opening, for directly accessing the mother's bared breast. It is a further object to maintain the integrity of the sterile surgical field throughout the procedure. It is a further object to open the portal and reclose the portal without lapse in sterile technique.

These objects, and others to become hereinafter apparent, are embodied in a surgical fenestration drape for the Cesarean delivery of a newborn from his/her mother comprising a drape sheet having a surgical opening and a portal. The sheet has a sterile-field side and a non-sterile-field side. The drape further comprises a first means for closing the portal, which is configured to be selectively manipulated from the non-sterile field side. The drape also comprises a second means for closing the portal, this second means configured to be selectively manipulated from the sterile-field side. The portal remains closed by the first means for closing until birth when the first means is then withdrawn from the portal to provide a window for the newborn to be placed into skin-to-skin contact with the mother's chest. Thereafter, the portal is reclosed by the second means for closing to protect the integrity of the sterile-field throughout the remaining procedure.

In the preferred embodiment, the first means for closing comprises a first flap having a sterile-field side. The sterile-field side of the first flap is releasably fastened by hook-and-loop material to the non-sterile-field side of the drape sheet. Further, the second means for closing comprises a second flap fastened to the sterile-field side of the drape sheet by double-sided adhesive after extending it from a fan-folded storage configuration.

In an alternate embodiment, a method of achieving immediate skin-to-skin contact of a newborn with his/her mother during Cesarean delivery comprises the steps of providing the surgical fenestration drape sheet discussed above; covering the mother with the drape sheet so that the portal is located proximate to the mother's chest; manipulating the first flap from the non-sterile side to open the portal immediately upon birth of the newborn; handing the newborn through the portal from the sterile-field side to rest in skin-to-skin contact with the mother's chest; and manipulating the second flap to reclose the portal from the sterile-field side while maintaining sterile-field integrity. The surgical procedure may then continue without interruption pursuant to this method.

As this is not intended to be an exhaustive recitation, other embodiments may be learned from practicing the invention or may otherwise become apparent to those skilled in the art.

DESCRIPTION OF THE DRAWINGS

Various other objects, features and attendant advantages of the present invention will become fully appreciated as the same becomes better understood through the accompanying drawings and the following detailed description, in which like reference characters designate the same or similar parts throughout the several views, and wherein:

FIG. 2 is a perspective view with the newborn after delivery showing the opened first flap in partial hidden line and the mother in phantom line;

FIG. 3 is a perspective view with the newborn in skin-to-skin contact under the closed second flap showing the portal and the newborn in hidden line and the mother in phantom line;

DETAILED DESCRIPTION OF THE PREFERRED EMBODIMENT

Figure 1:
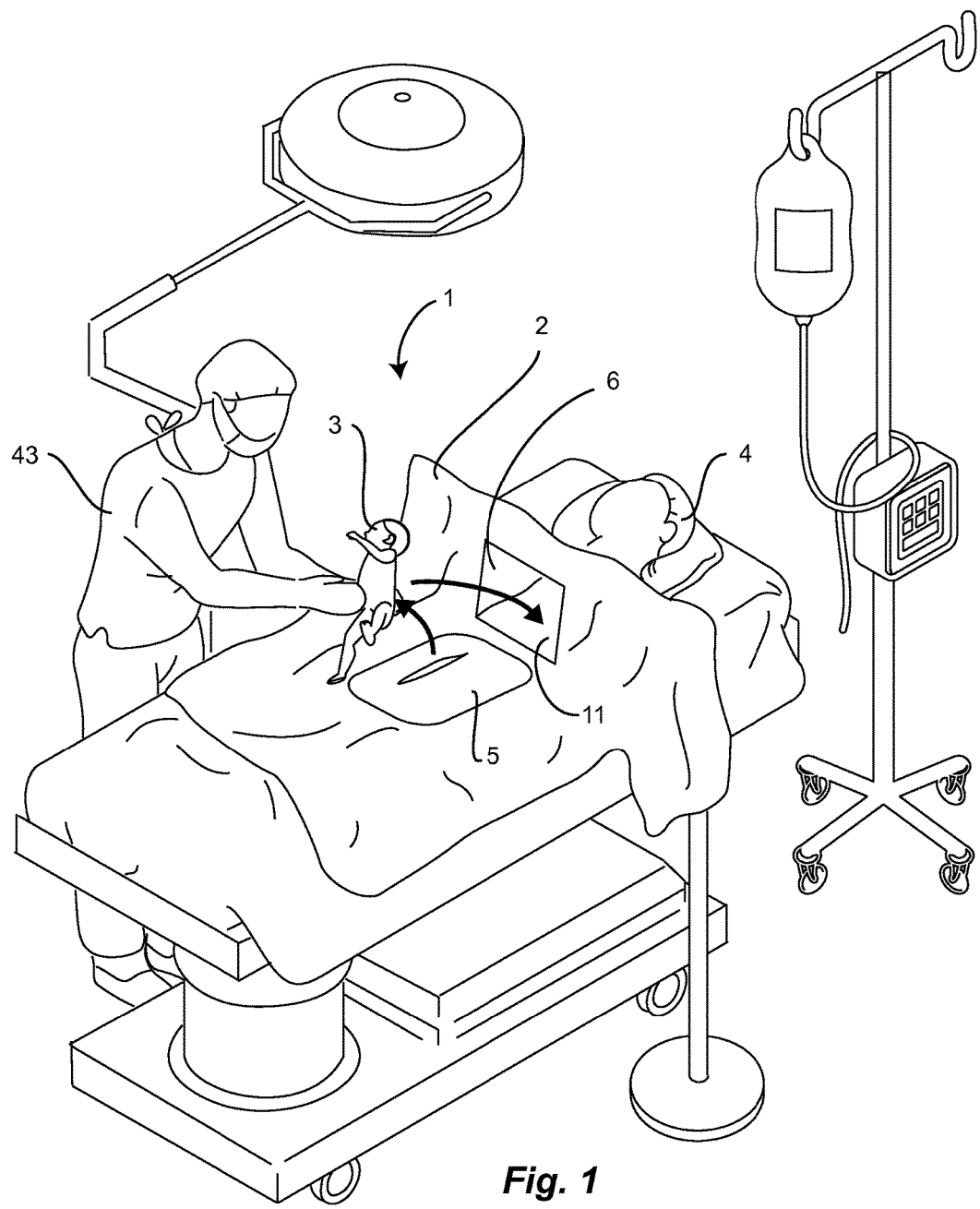
FIG. 1 is a sketch showing a delivery scene using the fenestration drape of the present invention.
Figure 7:
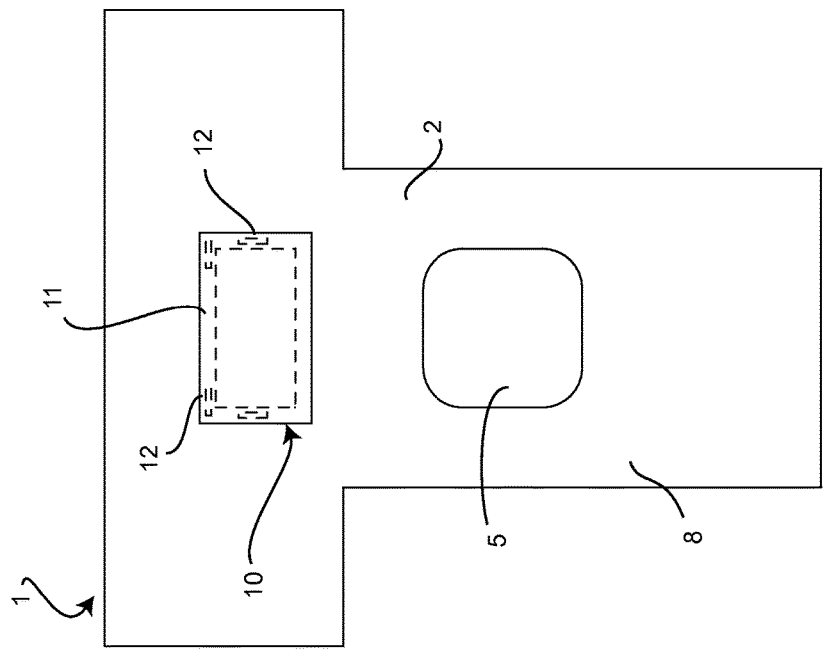
FIG. 7 is a plan view of the bottom of the drape showing the first flap closed with the portal and the hook-and-loop fasteners in hidden line.

As best shown in FIGS. 1-3, a surgical fenestration drape 1 for a Cesarean procedure delivering a newborn 3 from his/her mother 4 comprises a drape sheet 2, a portal 6, a first means for closing 10 the portal 6 and a second means for closing 20 the portal 6. The first means 10 and the second means 20 are used with sterile techniques to maintain a sterile-field barrier defined by a sterile-field side 7 (FIGS. 4 and 5) of the drape sheet 2 opposed by a non-sterile field side 8 (FIGS. 6 and 7). The portal 6 is an opening through the drape sheet 2, generally positioned to the chest-side of a surgical opening 5 located over the abdomen. The purpose of the portal 6 is to give immediate access for skin-to-skin contact (SSC) between the newborn 3 and the mother 4 to receive the benefits enumerated above.

In the preferred embodiment, the first means for closing 10 comprises a first flap 11, as shown in FIGS. 6 and 7. The first flap 11 also has a sterile-field side 13. The sterile-field side 13 of the first flap 11 is attached at the non-sterile field side 8 of the drape sheet 2 along one edge proximate the abdomen to hingingly flap down on a bared chest 9 of the mother 4 (FIG. 2). In a particularity, the first flap 11 is releasably held in place by hook-and-loop material 12, or otherwise by any known releasable attachment means, to cover the portal 6 until birth. Immediately following birth, the first flap 11 is released using sterile technique to lay it upon the bared chest 9 in the non-sterile field side 8 and provide thereby a sterile-field extension for placement thereon of the newborn 3.

Figures 4, 5:
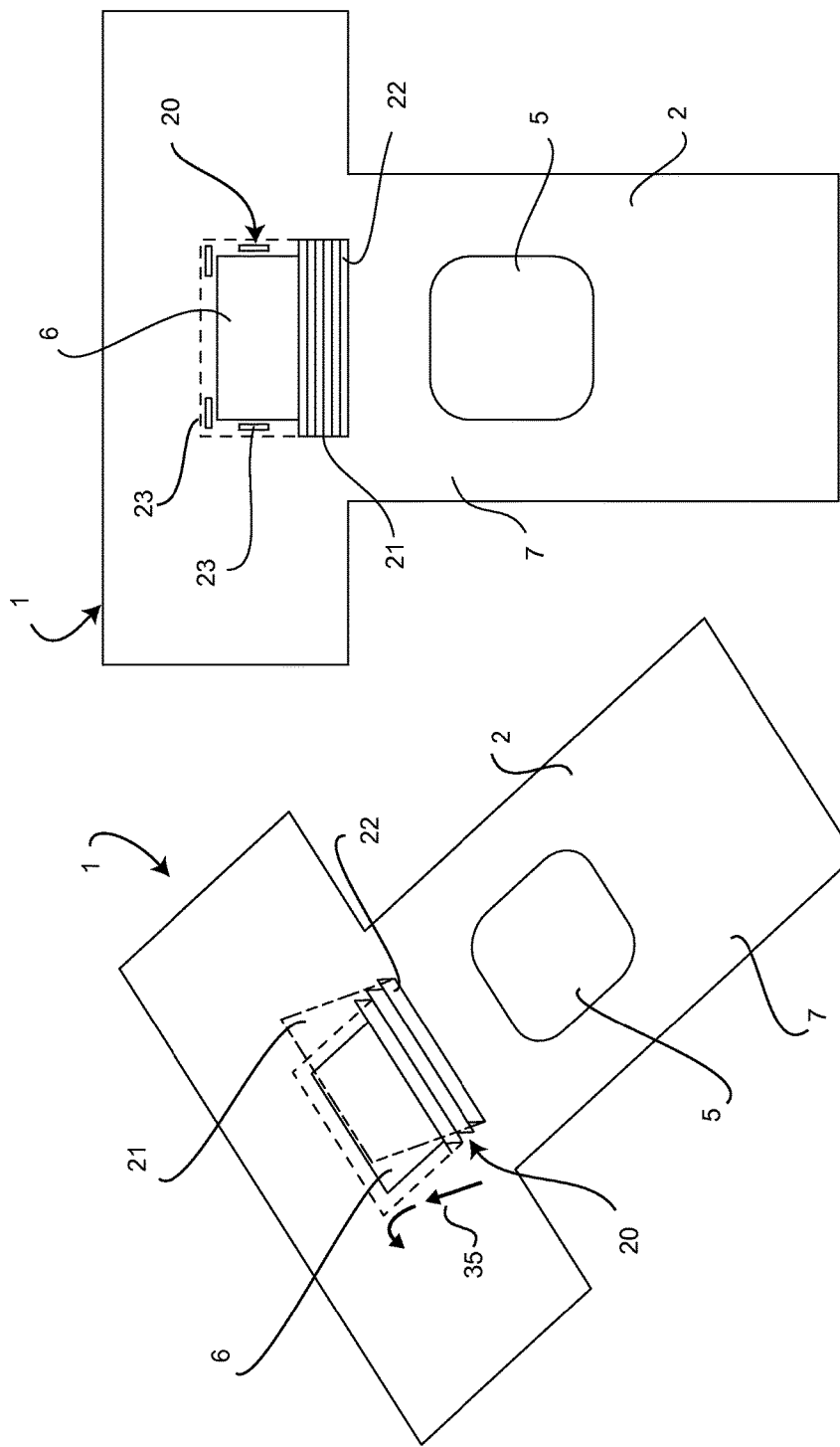
FIG. 4 is a perspective view of the top of the drape with the second flap shown in fan-folded configuration, and in extended configuration by phantom line, with the first flap shown in hidden line.
FIG. 5 is a plan view of the top of the drape showing the fan-folded second flap and the double-sided adhesive with the first flap shown in hidden line.
Figure 6:
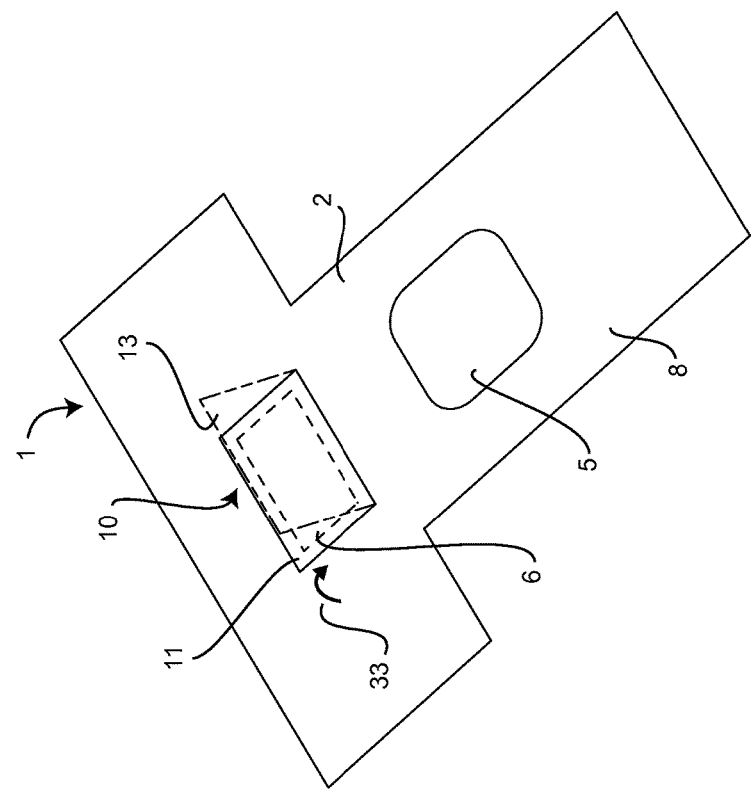
FIG. 6 is a perspective view of the bottom of the drape showing the first flap closed, and opened in phantom line, with the portal shown in hidden line.

Additionally, the second means for closing 20 comprises a second flap 21, as shown in FIGS. 4 and 5. The second flap 21 remains in a fan-folded conformation 22 until released therefrom after the newborn 3 is handed through the portal 6 from the sterile-field side 7 to be placed on the laid-open first flap 11. In a particularity, the second flap 21 is secured in place over the portal 6 (FIG. 3), thereby closing it to maintain sterile barrier, by double-sided adhesive 23, or otherwise by any known bonding means.

The drape sheet 2, the first flap 11 and the second flap 21 may be comprised of one or more laminations of a nonwoven material with poly film. In one particularity, the lamination may comprise a combination of spun-bonded and melt-bonded layers, otherwise known as SMS. In another particularity, the composition may comprise a moisture-impervious tri-laminate of SMS/Poly/SMS. The first and second flaps may be hingeably attached to the drape sheet by any known bonding means.

Figure 8:
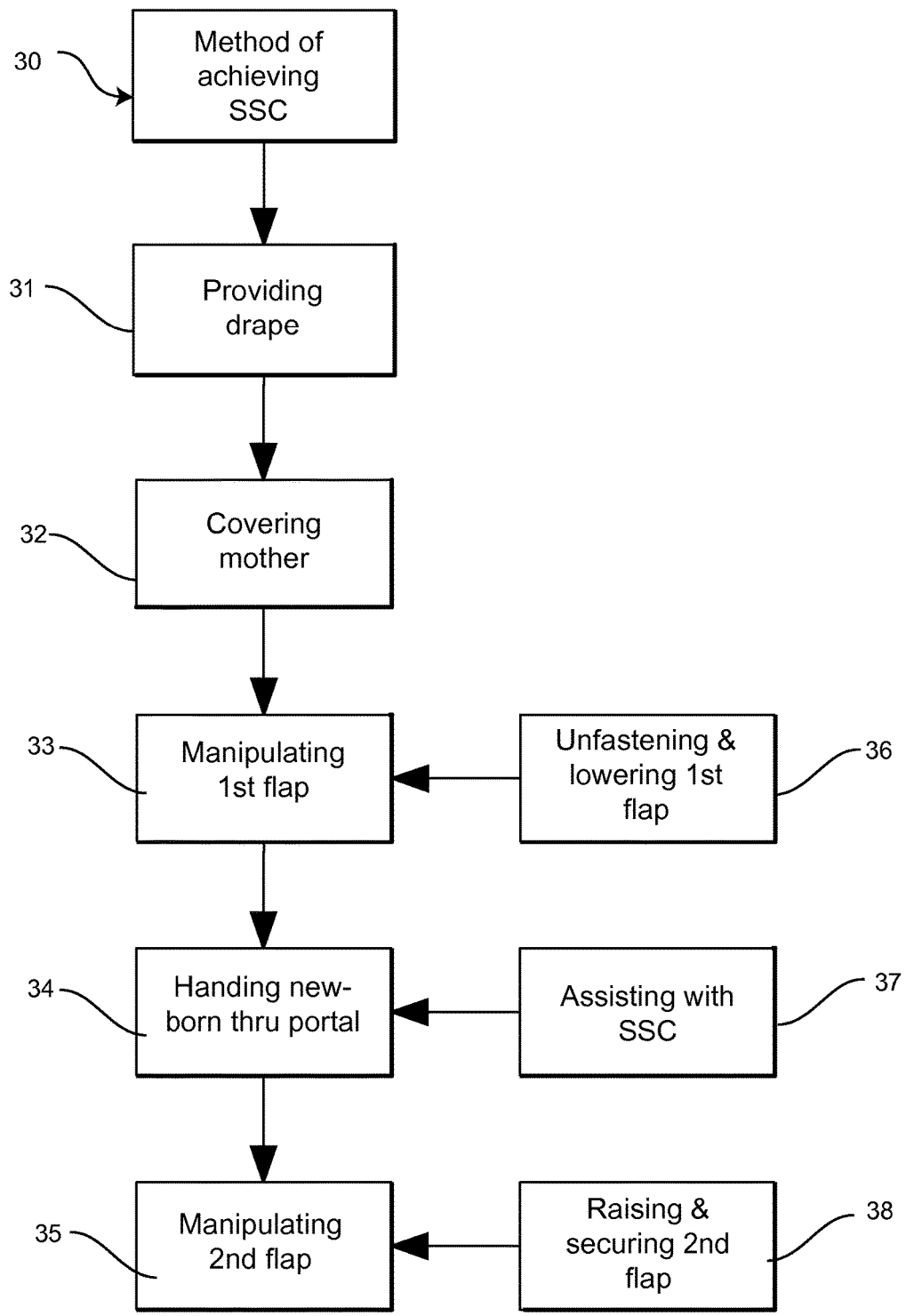
FIG. 8 is a schematic of the method of the present invention.

In an alternate embodiment shown in FIG. 8, a method of achieving immediate SSC 30 of a newborn 3 with his/her mother 4 during Cesarean delivery comprises:

Step 31: Providing a drape sheet 2 having a surgical opening 5 and a portal 6, said sheet having a sterile-field side 7 and a non-sterile field side 8, said portal closed by a first flap 11 before birth and by a second flap 21 after birth;

Step 32: Covering the mother 4 with the drape sheet 2 so that the portal 6 is located proximate to the mother's bared chest 9;

Step 33: Manipulating the first flap 11 from the non-sterile field side 8 to open the portal 6 immediately upon birth of the newborn 3 (FIG. 6);

Step 34: Handing the newborn 3 through the portal 6 from the sterile-field side 7 to rest in SSC with the mother's chest 9 (FIG. 2); and Step 35: Manipulating the second flap 21 to reclose the portal 6 from the sterile-field side 7, thereby and there through maintaining sterile-field integrity and allowing continuation of post-delivery procedure without interruption (FIG. 4).

In one particularity, the step 33 further comprises:

Step 36: Unfastening and lowering the first flap 11 onto the mother's bared chest 9, whereby the sterile field is extended through the portal 6, by a first assisting person 38 (not shown) positioned on the non-sterile side 8.

In another particularity, the step 34 further comprises:

Step 37: Assisting the mother 4 and the newborn 3 with skin-to-skin contact after an obstetrician 43 (FIG. 1) passes the newborn through the portal 6 onto the first flap 11 and the mother's bared chest 9.

In another particularity, the step 35 further comprises:

Step 38: Raising and securing a fan-folded second flap 22 to and onto the portal 6, whereby integrity of the sterile field is maintained throughout subsequent procedure, by a second assisting person 42 (not shown) positioned on the sterile side 7.

It is to be understood that the invention is not limited in its application to the details of construction, to the arrangements of the components and to the method of using set forth in the preceding description or illustrated in the drawings. For example, the first flap 11 may be transparent so that the mother may see the birth happening. Also, it is to be understood that the phraseology and terminology employed herein are for the purpose of the description and should not be regarded as limiting.

What is claimed is:

1. A surgical fenestration drape for the Cesarean delivery of a newborn, the drape comprising:
   a drape sheet having a surgical opening and a portal, said sheet having a sterile field side and an opposite non-sterile-field side;
   a first means secured to a portion of the non-sterile field side of the drape, the first means being configured for closing the portal, said first means configured to be selectively manipulated from the non-sterile field side; and
   a second means secured to a portion of the sterile field side of the drape, the second means being configured for closing the portal, said second means configured to be selectively manipulated from the sterile-field side;
   whereby, the portal is configured for closing by the first means until birth, when said first means is configured to be withdrawn from the portal while a portion of the first means remains attached to the non-sterile field side of the drape sheet to provide a window for the newborn to be placed into skin-to-skin contact with the mother's chest, and thereafter the second means is configured to close the portal, the sterile field side and a portion of the first means configured to maintain the integrity of the sterile-field throughout ensuing procedure.

2. The drape of claim 1, wherein the first means for closing comprises a first flap having a sterile-field side, the sterile-field side being releasably fastened to the non-sterile-field side of the drape sheet prior to birth.

3. The drape of claim 2, wherein the second means for closing comprises a second flap fastened to the sterile-field side of the drape sheet, the second flap stored in a fan-folded conformation until extended for reclosing the portal after birth.

4. The drape of claim 3, wherein the first flap is fastened with hook-and-loop material and the second flap is fastened by double-sided adhesive after the extension thereof.

5. The drape of claim 3, wherein the drape sheet and the first and second flaps are comprised of non-woven laminations with poly film, the non-woven laminations further comprising spunbonded and melt-blown layers in a trilaminate construction that is moisture-impervious.

6. The drape of claim 1, wherein, when said first means is configured to be withdrawn from the portal while a portion of the first means remains attached to the non-sterile field side of the drape sheet, the withdrawn portion of said first means is configured for placement on a chest of the mother to provide a surface for the newborn to be laid.

7. A surgical drape, comprising:
   a drape sheet including a first side, a second side, and at least one opening extending from the first side to the second side;
   a first flap configured to close the at least one opening, the first flap configured to be selectively manipulated from the first side of the drape sheet; and
   a second flap configured to close the at least one opening, the second flap being configured to be selectively manipulated from the second side of the drape sheet;
   wherein the drape sheet is in:
      a first state, prior to a birth of a newborn, in which the first flap covers the at least one opening;
      a second state, after the birth of the newborn, in which the first flap is withdrawn from the at least one opening and the newborn is passed through the at least one opening to a mother of the newborn; and
      a third state, after the newborn has been passed to the mother, in which the second flap covers the at least one opening; and
   wherein a sterile environment is present when the drape sheet is in each of the first, second, and third states.

8. The surgical drape of claim 7, wherein the first side of the drape sheet is non-sterile, and the second side of the drape sheet is sterile.

9. The surgical drape of claim 8, wherein the first flap includes a sterile side, the sterile side of the first flap being releasably fastened to the non-sterile side of the drape sheet when the drape sheet is in the first state; and
   wherein a sterile environment is formed by the sterile side of the drape sheet and the sterile side of the first flap when the drape sheet is in each of the first, second, and third states.

10. The surgical drape of claim 8, wherein the second flap is fastened to the sterile side of the drape sheet; and
   wherein the second flap is in a folded configuration when the drape sheet is in the first state, and in an extended configuration for closing the at least one opening when the drape sheet is in the third state.

11. The surgical drape of claim 10, wherein the second flap is secured to the second side of the drape sheet by double-sided adhesive after the second flap is in the extended configuration.

12. The surgical drape of claim 7, wherein the first flap is secured to the first side of the drape sheet with a hook-and-loop material.

13. The drape of claim 7, wherein the drape sheet and the first and second flaps are comprised of non-woven laminations with poly film, the non-woven laminations further comprising spun-bonded and melt-blown layers in a tri-laminate construction that is moisture-impervious.

14. The drape of claim 7, wherein the at least one opening comprises a plurality of openings, the plurality of openings including at least:
 a portal configured to provide a passage for passing the newborn to the mother when the drape sheet is in the second state; and
 a surgical opening to provide a passage for the newborn to be retrieved from a womb of the mother during a Cesarean section surgical procedure when the drape sheet is in the first state.

15. The drape of claim 14, wherein the portal is positioned proximate a chest area of the mother; and
 wherein the surgical opening is positioned to at least partially overlie a stomach area of the mother.

16. The drape of claim 7, wherein, when said first flap is in the second state, the withdrawn portion of said first flap is configured for placement on a chest of the mother to provide a surface for the newborn to be laid.

17. A method of using a surgical drape during Cesarean delivery to achieve immediate skin-to-skin contact of a newborn with a mother of the newborn, the method comprising:
 positioning a surgical drape on a mother such that at least one opening of the surgical drape is configured proximate a chest area of the mother, the at least one opening of the surgical drape being closed by a first flap of the surgical drape;
 manipulating the first flap from a first, non-sterile side of the surgical drape so that at least one opening is opened upon delivery of a newborn by the mother;
 passing the newborn through the at least one opening until the newborn is positioned on the chest area of the mother; and
 manipulating a second flap of the surgical drape from a second, sterile side of the surgical drape to close the at least one opening when the newborn is positioned on the chest area of the mother
 wherein a sterile environment is maintained throughout the method.

18. The method of claim 17, wherein manipulating the first flap from a first, non-sterile side of the surgical drape so that at least one opening is opened upon delivery of a newborn by the mother further includes:
 releasing the first flap from the at least one opening from the first, non-sterile side of the surgical drape upon the delivery of the newborn by the mother; and
 lowering the first flap onto the chest area of the mother such that a sterile side of the first flap is exposed on top of the chest area.

19. The method of claim 18, further including:
 placing the newborn onto the sterile side of the first flap, thereby establishing immediate skin-to-skin contact between the newborn and the mother.

20. The method of claim 19, wherein manipulating a second flap of the surgical drape from a second, sterile side of the surgical drape to close the at least one opening when the newborn is positioned on the chest area of the mother further includes:
 raising the second flap from the second, sterile side of the surgical drape upon the newborn being placed onto the sterile side of the first flap; and
 attaching the second flap to the second, sterile side of the surgical drape such that the second flap closes the at least one opening.

* * * * *